US 6,589,755 B1

(12) United States Patent
Ganu

(10) Patent No.: US 6,589,755 B1
(45) Date of Patent: Jul. 8, 2003

(54) ASSAY FOR QUANTIFYING ARTHRITIC CONDITIONS

(75) Inventor: Vishwas Ganu, Bridgewater, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/242,427
(22) PCT Filed: Aug. 8, 1997
(86) PCT No.: PCT/EP97/04316
  § 371 (c)(1),
  (2), (4) Date: Feb. 16, 1999
(87) PCT Pub. No.: WO98/07035
  PCT Pub. Date: Feb. 19, 1998

Related U.S. Application Data
(60) Provisional application No. 60/024,041, filed on Aug. 15, 1996.
(51) Int. Cl.[7] .................... G01N 33/53; G01N 33/537
(52) U.S. Cl. .................... 435/7.92; 435/6; 435/7.1;
    435/7.92; 435/69.1; 435/69.3; 436/538;
    436/539; 436/548; 436/166; 436/174; 436/175;
    436/176; 436/177; 436/178
(58) Field of Search .................... 435/6, 7.1, 7.92,
    435/69.1, 69.3, 70.1; 436/501, 503, 539,
    538, 548, 808, 166, 174–178; 530/387.1,
    288.1, 388.22, 388.25, 388.7, 388.85, 390.5

(56) References Cited
U.S. PATENT DOCUMENTS
4,610,960 A * 9/1986 Mosher .................... 435/7
4,778,768 A   10/1988 Heinegärd et al. .......... 436/501
5,766,591 A * 6/1998 Brooks et al. ............. 424/184
5,948,692 A * 9/1999 Miyauti et al. ............ 436/501

FOREIGN PATENT DOCUMENTS
WO    96/01847    1/1996

OTHER PUBLICATIONS

Oldberg et al., COMP (Cartilage Oligomeric Matrix Protein) is structurally related to the Thrombospondins, The Journal of Biological Chemistry vol. 267 (31) 22346–22350 (1992).*

(List continued on next page.)

Primary Examiner—Christopher L. Chin
Assistant Examiner—Gailene R. Gabel
(74) Attorney, Agent, or Firm—David E. Wildman

(57) ABSTRACT

The present invention is drawn to a novel and newly discovered low molecular weight protein fragments that are degradation products of COMP and have a molecular weight of about 14–33 kilodaltons and polyclonal and monoclonal antibodies to the new COMP fragment and other known COMP fragments of molecular weight 67–80 kDa and 150–250 kDa, and thrombospondin fragments (collectivvly referred to as "ADP") as well as an assay to measure the level of ADP comprising: (1) incubating a body fluid sample, which has been obtained from an arthritis patient, under reducing or non-reducing conditions; (2) incubating the body fluid sample with an anti-ADP antibody; and (3) measuring the level of bound anti-ADP antibody in the body fluid sample. Also disclosed is an assay to measure the ratio of ADP to KS as a diagnostic measure of arthritic disease.

6 Claims, 4 Drawing Sheets

OTHER PUBLICATIONS

Saxne et al., "Cartilage Oligomeric Matrix Protein: A Novel Marker Of Cartilage Turnover Detectable in Synovial Fluid And Blood", British Journal of Rheumatology, vol. 31, pp. 583–591, (1992).

Champion et al., Arthritis and Rheumatism, vol. 34, No. 10 (1991).

Di Cesare et al., The Journal of Orthopaedic Research, vol. 14, No. 6, pp. 946–955 (1996).

Forslind et al., British Journal of Rheumatology, vol. 31, pp. 593–598 (1992).

Newton et al., Genomics, vol. 24, pp. 435–439 (1994).

Peterson et al., Annals of Rheumatic Diseases, vol. 56, pp. 64–67, (1997).

Sharif et al., British Journal of Rheumatology, vol. 34, pp. 306–310 (1995).

Thonar et al., Acta Orthop Scand (Suppl. 266), vol. 66, pp. 103–106.

Vilim et al., Archives of Biochemistry and Biophysics, vol. 341, No. 1, pp. 8–16 (1997).

* cited by examiner

SEQUENCE LISTING

```
<160> NUMBER OF SEQ ID NOS:  4

<210> SEQ ID NO 1
<211> LENGTH: 17
<212> TYPE: PRT
<213> ORGANISM: Homo sapiens

<400> SEQUENCE: 1

Cys Asn Asp Thr Ile Pro Glu Asp Tyr Glu Thr His Gln Leu Arg Gln
 1               5                  10                  15

Ala

<210> SEQ ID NO 2
<211> LENGTH: 14
<212> TYPE: PRT
<213> ORGANISM: Homo sapiens

<400> SEQUENCE: 2
```

-continued

```
Lys Asp Pro Arg Asn Val Gly Trp Lys Asp Lys Ser Tyr
  1               5                  10

<210> SEQ ID NO 3
<211> LENGTH: 17
<212> TYPE: PRT
<213> ORGANISM: Rat

<400> SEQUENCE: 3

Cys Asn Asp Thr Ile Pro Glu Asp Tyr Glu Arg His Arg Leu Arg Arg
  1               5                  10                  15

Ala

<210> SEQ ID NO 4
<211> LENGTH: 17
<212> TYPE: PRT
<213> ORGANISM: Cow

<400> SEQUENCE: 4

Cys Asn Asp Thr Ile Pro Glu Asp Tyr Gly Ala Gln Arg Leu Leu Gln
  1               5                  10                  15

Ala
```

ASSAY FOR QUANTIFYING ARTHRITIC CONDITIONS

This application is a National Stage, 371 of PCT/EP97/04316, filed Aug. 8, 1997, which claims the benefit of priority to US Provisional Application No. 60/024,041, filed Aug. 15, 1996.

FIELD OF THE INVENTION

The present invention relates to new low molecular weight protein fragments that are degradation products of the cartilage oligomeric matrix protein (COMP) unique antibodies to these fragments and methods of using such antibodies to measure the severity of arthritic conditions.

BACKGROUND OF THE INVENTION

Cartilage Oligomeric Matrix Protein (COMP) is a pentamer of molecular weight 435,000 that is part of the extracellular matrix of cartilage. Each monomer of about 87,000 is synthesized and secreted by cartilage chondrocytes. COMP is thought to constitute about 1 percent of the wet weight of cartilage. COMP is similar in structure to the members of the thrombospondin gene family. They are similar in the type 3 repeats and the C-terminal region. Thrombospondins, although similar in structure to COMP, have activities to regulate cell migration, growth and proliferation (such as vascular smooth muscle) and inhibit the growth of endothelial cells (Newton et al., (1994) Genomics 24: 435–439).

The physiological function of COMP is not known but its presence in the synovial fluid and serum has been correlated with osteoarthritis (Sharif et al., (1995) 34: 306–310) and rheumatoid arthritis (Forslind et al., Brit. J. Rheumatology, (1992) 31: 593–598). It has also been proposed as a marker of cartilage turnover in synovial fluid and blood (Saxne and Heinegard, D. (1992) Br. J. Rheumatology 31: 583–591). Moreover, the synovial fluids of rheumatoid arthritis patients that have high levels of COMP contain a 65 kilodalton fragment and possibly (under reducing conditions) traces of a lower molecular weight species (Saxne and Heinegard, D. (1992) Br. J. Rheumatology 31: 583–591). A recent study also demonstrated that the cartilage as well as the synovial fluid from patients with osteoarthritis and rheumatoid arthritis contain fragments ranging from 43 kDa, 67–94 kDa, 150–200 kDa (Dicesare P. E. et al., (1996) J. Orthopaedic Res. 14: 946–955).

Another cartilage matrix protein, cartilage matrix glycoprotein (CMGP), has been found in the serum of osteoarthritic dogs (Fife and Brandt (1989) J. Clin. Invest. 84: 1432–1439) but it has not been shown to be the result of cartilage breakdown. U.S. Pat. No. 4,778,768 discloses the correlation of cartilage damage and measurement of proteoglycan and fragments. The release of the G1 domain of proteoglycan increased with disease severity in rheumatoid arthritis but the larger region of glycosaminoglycan-rich region (CS/KS domain) decreased under the same conditions (Saxne and Heinegard, (1993) Arthritis Rheum. 35: 385–390). This demonstrates that it has until now been unpredictable whether fragments of a protein can predict a disease state.

Aggrecan is a proteoglycan residing in the cartilage. This protein consists of keratan sulfate (KS) side chains. In arthritis, aggrecan degradation products have been found in the synovial fluids of patients. One way of measuring aggrecan degradation products in the synovial fluid and serum is to quantify by an ELISA using antibodies that recognize keratan sulfate side chains (Thonar E J-M A et al., (1995) Acta Orthop. Scand (S266) 66: 103–106). Investigations in several laboratories could not confirm the usefulness in measuring serum KS in arthritic patients.

Thrombospondin (450 kDa) is a high molecular weight adhesive glycoprotein consisting of three identical monomers of molecular weight 150 kDa. It is found in the cartilage and is produced by articular chondrocytes (Miller and McDevitt (1988), Biochem. Biophys. Res. Comm. 153: 708–714). To date there are no reports which document the presence of thrombospondin or its degradation products in the synovial fluid of arthritic patients.

Quantification of serum COMP may have prognostic value for rheumatoid arthritis and osteoarthritis (M Sharif, Saxne T, Shepstone L, Kirwan J R, Elson C J, Heinegard D, Dieppe P A: Br J Rheumatol 34: 4, 306–10,1995.; Hansson B M, Carey D, Alini M, Ionescu M, Rosenberg L C, Poole A R, Heinegard D, Saxne T, J Clin Invest 95:1071–7, 1995). However, previous assays which quantify serum COMP do not allow determination of whether cartilage degradation is on-going in an arthritic patient.

Antigenic KS is present in elevated amounts in synovial fluid from human osteoarthritis joints (Shimozuru et al., Orthop. Trans. 20:419 1995). The levels of this and other markers of proteoglycan catabolism are highest during the pre-radiological stages of the disease and tend to drop with time, especially in joints exhibiting secondary inflammatory changes or loss of articular cartilage mass (see Thonar E J-M A et al., Sports medicine & arthroscopy review: chondral injuries (Ed. Andrish J. T). Raven Press, New York 1994: 13–29, for review). This makes interpretation of the data difficult. However, this difficulty can be circumvented by measuring additional markers and reporting the results as ratios of one marker to another (Thonar E J-M A et al., Acta Orthop. Scand. (Suppl 266) 66:103–106 1995). Interestingly, a recent report has claimed that the ratio of antigenic COMP to antigenic KS in the synovial fluid of the same patient may be useful in monitoring changes in cartilage macromolecue turnover (Peterson et al., (1997) Ann. Rheum. Disease 56: 64–67.)

Identification of new proteins or fragments of proteins (degradation products) or ratios of the different proteins or fragments whose presence in the synovial fluid and/or blood serum can be correlated with a disease state such as arthritis (osteoarthritis or rheumatoid arthritis) would be useful for diagnosis and treatment of such diseases. Moreover, the development of new antibodies and other molecules to detect such new proteins or fragments of proteins would allow easily utilized assays to be routinely applied for the diagnosis and treatment of patients with arthritis. For new drug development in arthritis there is a need to have assays to evaluate efficacy of the new drug on the cartilage matrix and a means to select patients for treatment therapies. The present invention has identified new low molecular weight fragments of the COMP protein that are correlated with the progression of arthritis, antibodies which bind to these fragments and assays to measure the severity of arthritis disease states by quantifying these fragments and other known COMP fragments and fragments of thrombospondin-1 ("TSP-1"). In our investigations using the anti-peptide antibody to the carboxy terminal of COMP, what was unforeseen is that specific breakdown products derived from the carboxyl terminal end of this molecule or a ratio of the breakdown products to KS would have diagnostic or prognostic value. It shows that the level of COMP is different than these C-terminal degradation products and reflect something different than the intact molecule. In addition, this antibody was found to recognize the other known COMP fragments. Moreover, this antipeptide antibody unexpectedly recognized the N-terminal 20 kDa fragment of bovine thrombospondin, and full-lenth human TSP-1. Since the N-terminal sequence of bovine and human thrombospondin are identical, this antibody is expected to recognize N-terminal 20 kDa fragment of human TSP-1.

SUMMARY OF THE INVENTION

The present invention is drawn to a group of novel and newly discovered low molecular weight protein fragments that are C-terminal degradation products of COMP. A first group, referred to herein as "LMW-COMP" fragments, have a molecular weight of about 14–33 kilodaltons on SDS-PAGE. Preferably, the LMW-COMP fragments have a molecular weight of about 30, 20, 18, 16 or 14 kilodaltons and most preferably the LMW-COMP is the predominant species of low molecular weight degradation products having an apparent molecular weight on SDS-PAGE electrophoresis of about 20 kilodaltons. This COMP fragment is produced in increasing amounts as the arthritis disease condition becomes more severe. These newly discovered C-terminal COMP fragments are only separated from other COMP components under reducing conditions and therefore their separation depends on assays wherein the separation of COMP fragments (if it occurs) is conducted under such reducing conditions. Another aspect of the present invention is polyclonal and monoclonal antibodies capable of binding to the new LMW-COMP fragments. The LMW-COMPs are recognized by antibodies, preferably monoclonal antibodies, to the amino acid polypeptide derived from at least the 17 amino acid carboxy terminus of COMP. These antibodies, upon Western blotting, detect another group of COMP C-terminal degradation fragments which have a molecular weight of from about 67 kDa to about 80 kDa and 150 kDa to 250 kDa and also cross-react with another arthritic degradation product which is a 20 kDa fragment of thrombospondin derived from the N-terminus of TSP-1. The LMW-COMP fragments, the 67–80 kDa and 220–250 kDa COMP fragments and the thrombospondin fragments are collectively referred to herein as "arthritic degradation products" or "ADP". Therefore the use of the term "arthritic degradation products" or "ADP" can refer to all three fragments described above together or one or more of the fragments alone. The antibodies which recognize and bind to these fragments are, therefore, referred to as "ADP antibodies". Still another aspect of the present invention is assay techniques to measure the level of ADP in various bodily fluids, preferably synovial fluid and serum.

A preferred embodiment of the assay aspect of the invention is an assay to measure the level of ADP comprising:

(1) incubating a body fluid sample, which has been obtained from an arthritis patient, under reducing or non-reducing conditions;

(2) incubating the body fluid sample with an anti-ADP antibody; and (3) measuring the level of bound anti-ADP antibody in the body fluid sample.

In a most preferred embodiment of the assay, the ADP are LMW-COMP fragments.

Optionally, the level of bound anti-ADP antibody in the body fluid sample can be compared to the level of bound anti-ADP antibody in the body fluid sample at a different time during diagnosis and/or treatment of the arthritis.

Yet another aspect of the present invention is directed to diagnostic assays for measuring the ratio of the arthritic degradation products to the level of KS in a bodily fluid sample derived from a patient, preferably synovial fluid, and serum samples, for diagnosis and/or treatment of arthritis.

DETAILED DESCRIPTION OF THE INVENTION

Figure 1:
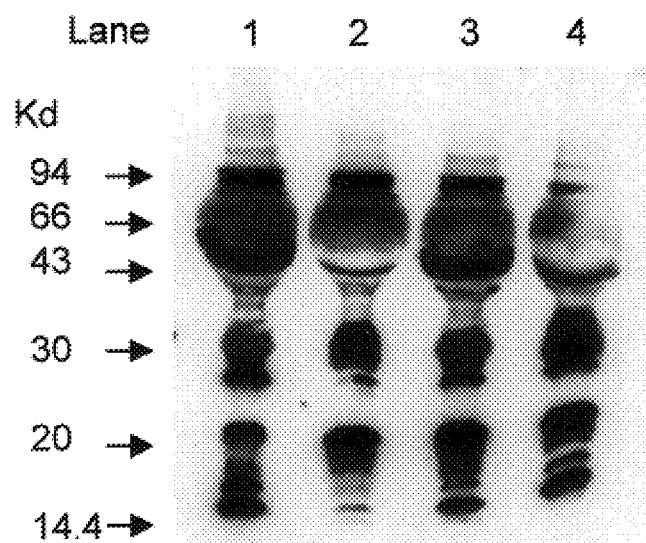
FIGS. 1 shows Western blot analysis of synovial fluid from patients with different arthritic conditions using rabbit anti-H741 antibody. Lane 5, Moderate RA; Lane 4, Psuedo gout; Lane 3, Gouty arthritis; Lane 2, Pseudo gout; Lane 1, Low mol. wt. markers: 97.4 kDa, 66.3 kDa, 45 kDa, 31 kDa, 21.5 kDa.

The present invention is drawn to a group of novel and newly discovered low molecular weight protein fragments that are C-terminal degradation products of COMP. The protein fragments are LMW-COMP fragments having a molecular weight of between 14 and 33 kDa. on SDS-PAGE. Preferably, the LMW-COMP fragments have a molecular weight of about 30, 20, 18, 16 or 14 kilodaltons and most preferably the LMW-COMP is the predominant species of low molecular weight degradation products having an apparent molecular weight on SDS-PAGE electrophoresis of about 20 kilodaltons. This COMP fragment is produced in increasing amounts as the arthritis disease condition becomes more severe. These newly discovered C-terminal COMP fragments are only separated from other COMP components under reducing conditions and therefore their separation depends on assays wherein the separation of COMP fragments (if it occurs) is conducted under such reducing conditions.

Another aspect the present invention is directed to polyclonal and monoclonal antibodies to the new LMW-COMP fragment. These antibodies also cross react with another group of COMP C-terminal degradation fragments which have a molecular weight of from about 67 kDa to about 80 kDa and from about 150 kDa to about 250 kDa, and also cross-react with another arthritic degradation product which is a 20 kDa fragment of TSP-1 derived from the N-terminus of TSP-1. Suitable body fluids include any body fluid that is obtained from an arthritic patient. Examples of suitable body fluid include blood, serum, saliva, urine, synovial fluid, etc. The preferred body fluids are synovial fluid, blood serum and urine with synovial fluid and serum being most preferred. Synovial fluid is the most likely to have the highest levels of ADP. Arthritis patients are those that have been diagnosed by an attending clinician or who have the symptoms associated with arthritis. Arthritis includes both osteoarthritis and rheumatoid arthritis. ADP may also be found in association with cartilage degradation as a result of traumatic joint or bone injury. This includes bone breakage, torn cartilage, joint dislocation and the like.

The ADP can be isolated or separated from COMP and other COMP degradation products using known separation techniques. These include gel filtration chromatography, electrophoresis, and selective precipitation. It is important that the separation technique for separating the 14–33 kilodalton fragments be conducted under reducing conditions. Apparently, the LMW-COMP has at least a disulfide bond with itself or another part of the COMP protein so that reduction of the bond frees the LMW-COMP and it can be separated and detected. Reducing conditions typically involve a solution of the body fluid to which a reducing agent has been added. Suitable reducing agents include those known in the art to reduce disulfide bonds. Preferred reducing agents include dithiothreitol (DTT), beta mercaptoethanol, cysteine and ascorbic acid. The reducing agent is used in concentration sufficient to facilitate reduction of the disulfide bonds, that is in a concentration to allow at least a 1:1 ratio of disulfide bonds:reducing agent. Typically 0.1–100 mM of reducing agent is sufficient and the incubation with the reducing agent takes place for from about 30 seconds to about 30 minutes and at a temperature of from about 25–45° C. Preferably the incubation takes place for about 5 minutes and at about 37° C. After exposure of the body fluid solution to a reducing agent for the desired amount of time during separation, the excess reducing agent can be inactivated using a reducing agent inactivating substance such as iodoacetamide or n-ethyl maleimide. This inactivation step is particularly important when ELISA assay is used as the detection or measurement technique. The concentration of the reducing agent inactivating substance is in excess of the concentration of reducing agent added to the body fluid previously, preferably at least about twice as much. Therefore, if the concentration of reducing agent in the body fluid is 1 mM, the concentration of the reducing agent inactivating substance is at least 2 mM. Optionally, the body fluid solution may be treated with a substance to reduce the viscosity of the body fluid (a viscosity reducer). This is particularly useful when the body fluid is synovial fluid and the detection of LMW-COMP is by Western blotting. Protease free Streptomyces hyaluronidase is one suitable viscosity reducing substance and others are known in the art. Another optional treatment of the body fluid is selective precipitation of proteins in the body fluid to enhance low molecular weight fragments of COMP. Selective precipitation can be performed using, for example, 30% ammonium sulfate or 20% polyethylene glycol.

Whether or not the LMW-COMP is isolated or separated from COMP and other COMP degradation products, the measurement, detection or quantification of the LMW-COMP is important. If separation does take place, detection allows confirmation of the extent of purity. If separation does not take place, detection allows the amount of LMW-COMP to be measured as an indication of the severity of a disease when one manifestation of the disease is the production of LMW-COMP. The present invention utilizes newly produced antibodies to the LMW-COMP as a detection technique. These antibodies cross-react with the 67–80 kDa fragment and the 150–250 kDa fragment and with the N-terminal end of TSP-1, thus they are referred to as "ADP antibodies". This is unexpected because, as stated previously, the amino acid sequences of C-terminal COMP and that of N-terminal TSP-1 are entirely different. The 67–80 kilodalton -COMP fragment, which is known per se, is predominant under non-reducing conditions and possess the C-terminal end of the full-length COMP fragment and is found in synovial fluid and from human osteoarthritic cartilage in culture. This is demonstrated using human cartilage digested with matrix metalloproteinases (MMPs), followed by quantitation of the 67–80 kDa fragment in the medium.

The antibodies thus generated can be used to detect ADP via, for example, Western blotting or ELISA, both of which are well known in the art. Because of the susceptibility of antibodies to reducing agents, it may be necessary to inactivate any excess reducing agent used to liberate the ADP with a reducing agent inactivating substance prior to exposure or incubation of the body fluid to an anti-LMW-COMP antibody. Moreover, measurement of ADP by ELISA can be conducted without reducing conditions because it is the quantity of immunoreactivity, not the molecular weight that is measured. An ELISA may be employed to monitor efficacy of drugs that will inhibit the formation of the 67–80 kDa and 150–250 kDa COMP fragment. It has surprisingly been found that the 67–80 kDa COMP fragment is produced upon degradation by serine metalloproteinase as well as matrix metalloproteinases. Therefore, this assay has the potential to monitor efficacy of inhibitors of MMP and other unidentified enzymes both in vitro and in vivo. The ELISA assay described hereinafter may be more sensitive in predicting COMP composition when compared with the ELISA using a polyclonal antibody. In addition, this assay points out the possible different mechanisms of cartilage degradation depending upon nature and disease severity.

The antibodies to ADP can be obtained in a variety of ways. The isolated LMW-COMP can be used as an immunogen to raise antibodies in an test animal. If the antibodies are raised in mice, monoclonal antibodies can be prepared using known techniques. Moreover, chimeric antibodies and humanized antibodies can also be made by those of skill in the art. Otherwise, the polyclonal antibodies raised in the animals can be used. Also, instead of using the full length LMW-COMP as the immunogen, shorter segments of the LMW-COMP such as the C-terminal peptide sequence can be used as can synthetic peptides having a sequence corresponding to a portion of the LMW-COMP. Preferred synthetic peptides are preferably from the C-terminal region of COMP. Preferred synthetic peptides are peptides H741, and H669 containing the specified residues from the full length COMP.

$Cys^{741}$-Asn-Asp-Thr-Ile-Pro-Glu-Asp-Tyr-Glu-Thr-His-Gln-Leu-Arg-Gln-$Ala^{757}$-COOH (H741) (SEQ ID NO:1)

$Lys^{669}$-Asp-Pro-Arg-Asn-Val-Gly-Trp-Lys-Asp-Lys-Lys-Ser-$Tyr^{683}$-CONH2 (H669) (SEQ ID NO:2)

The resulting antibodies are designated antibody H741 and antibody H669, respectively and the cells producing them are designated hybridoma H741 and H669, respectively.

Further preferred synthetic peptides are from the C-terminal region of rat COMP and from the C-terminal region of bovine COMP.

Rat-$NH_2$-$Cys_{737}$-Asn-Asp-Thr-Ile-Pro-Glu-Asp-Tyr-Glu-Arg-His-Arg-Leu-Arg-Arg-$Ala_{755}$COOH (SEQ ID NO:3) (Hrat), and Bovine-$NH_2$-Cys-Asn-Asp-Thr-Ile-Pro-Glu-Asp-Tyr-Glu-Ala-Glu-Arg-Leu-Leu-Gln-AlaCOOH (SEQ ID NO:4) (Hbov).

The resulting antibodies likewise are designated antibody Hrat and antibody Hbov, respectively and the cells producing them are designated hybridoma Hrat and Hbov, respectively. It is important to note that the antibodies raised to the peptides described above, upon Western blotting, detect all ADP fragments. An antibody that does not recognize COMP was unable to detect these ADP fragments. These observations suggested that these proteins, the ADP fragments, in the synovial fluid could be the degradation products of COMP. Moreover, it has been found that the C-terminal anti-peptide antibody recognizes ADP fragments that were not recognized in a Western analysis by polyclonal antibody to COMP.

A particularly preferred method of measuring the amount of ADP in a body fluid is the assay aspect of the present invention. Such an assay to measure the level of ADP comprises:
(1) incubating a body fluid sample, which has been obtained from an arthritis patient, under reducing or non-reducing conditions;
(2) incubating the body fluid sample with an anti-ADP antibody; and
(3) measuring the level of bound anti-ADP antibody in the body fluid sample.

In a preferred embodiment of the assay ADP is LMW-COMP, and the body fluid is synovial fluid or serum. In the event reducing conditions are used, the reducing conditions are dithiothreitol or mercaptoethanol at about 1 mM for about 5 minutes at 37° C. The preferred anti ADP antibody is produced in rabbits sensitized with peptide H741. The preferred method of measuring the level of bound anti-LMW-COMP antibody is Western blotting following electrophoresis. When Western blotting is used as the measurement technique, it is usually advisable to inactivate the excess reducing agent with a reducing agent inactivating substance prior to beginning the incubation of the body fluid sample with an anti-LMW-COMP antibody.

The present invention also includes a kit for performing the assay aspect of the invention. Such a kit includes a solution or mixture of one or more LMW-COMP with a molecular weight of from about 14 to about 33 kilodaltonsand/or an anti-ADP antibody. The kit may additionally contain vials or vessels for incubating a body fluid sample, viscosity reducer, a reducing agent inactivating substance and or separation materials.

An immunoassay was developed using antibodies to the C-terminal 17-amino acid sequence (SEQ ID NO:1) of COMP, and antigenic COMP in the human synovial fluid from arthritic patients was quantified. When the antigenic contents of COMP in the synovial fluid from a arthritic patients at different stages of disease were compared with the contents of proteoglycan (measured by KS ELISA) in those same synovial fluids, a distinct COMP antigen contents/KS ratio was obtained for patients in each disease group. Thus, measurement of COMP content using this C-terminal derived antibody to COMP is useful in the diagnosis and monitoring of arthritic patients.

In another aspect of the present invention there is disclosed an assay for measuring an additional marker of cartilage breakdown and reporting the results as a ratio of one marker to another. In this assay the ADP are measured as described above. The amount of KS, a glycosaminoglycan which is predominantly present in the proteoglycan of cartilage, is then determined using methods known per se (Campion, G. V. et al., Arthritis and Rheum. 34(10): 1254–1259 (1991)). The ADP values are then compared with KS values for the measurement of the ratio of ADP to KS value. This ratio is indicative of the stage of arthritic condition and one objective of chondroprotective therapy is to prevent the increase in the ratio of ADP/KS. In a preferred embodiment several body fluid samples are assayed for the level of COMP and LMW-COMP and KS therein and a mean value is taken for each. The mean values are then used to determine the ratio of these fragments to one-another.

The present invention is useful for the measurement of ADP in the prognosis, diagnosis and treatment of arthritis diseases. As a measurement of the severity of an arthritic condition, the present invention allows attending clinicians optimize treatment and administration of pharmaceuticals in the treatment of arthritis. By comparing the levels of ADP prior to or early in treatment with the levels during or after treatment allows the clinician to monitor the effectiveness of the treatment and adjust the administration of pharmaceuticals or other treatment. The present invention can also be used diagnose the stage of an arthritis condition by tracking the levels of ADP over a period of time. The change in ADP levels can indicate whether an arthritic condition is increasing, decreasing or stabilized. This information can also allow a better course of treatment to be designed and administered.

The ADP of this invention are useful as molecular markers in diagnosing arthritic conditions. For example, isolated LMW-COMP fragments can be run parallel on an electrophoresis gel or gel filtration column with ADP from a sample as an indication of the distribution of COMP fragments in the sample. In this case the sample can be a body fluid sample or it can be from a cell or tissue culture, particularly a cell or tissue culture that produces COMP (e.g., chondrocytes and the like).

EXAMPLES

Example 1

Preparation of Anti-peptide Antibody to Synthetic Peptides Derived From C-terminal Region of COMP Each of the synthetic peptides bearing a sequence corresponding to the residues in human COMP polypeptide beginning with $Cys^{741}$-Asn-Asp-Thr-Ile-Pro-Glu-Asp-Tyr-Glu-Thr-His-Gln-Leu-Arg-Gln-$Ala^{757}$-COOH (SEQ ID NO:1) (H741), were coupled to Keyhole limpet hemocyanine via N-terminal cysteine, and antibodies in rabbits were prepared using previously.established methods (Briand et al., (1985) J. Immunol. Methods 78: 59–69). The antibody was affinity purified using sepharose-peptide affinity columns. The second synthetic peptide of human COMP $Lys^{669}$-Asp-Pro-Arg-Asn-Val-Gly-Trp-Lys-Asp-Lys-Lys-Ser-$Tyr^{683}$-CONH2 (SEQ ID NO:2) (H669) was coupled to KLH via glutaraldehyde method (Briand et al., (1985) J. Immunol. Methods 78: 59–69), and rabbit antibodies were prepared as described above.

Monoclonal antibodies are prepared using the H741, and H669 peptides according to established methods (Kohler and Milstein, (1975) Nature 256: 495–497; Yelton and Sharff (1981) Ann. Rev. Biochem. 50: 657–680). The resulting antibodies are designated antibody H741 and antibody H669, respectively and the cells producing them are designated hybridoma H741 and H669, respectively. Moreover, chimeric antibodies and humanized antibodies can also be made by those of skill in the art.

Example 2

Figure 2:
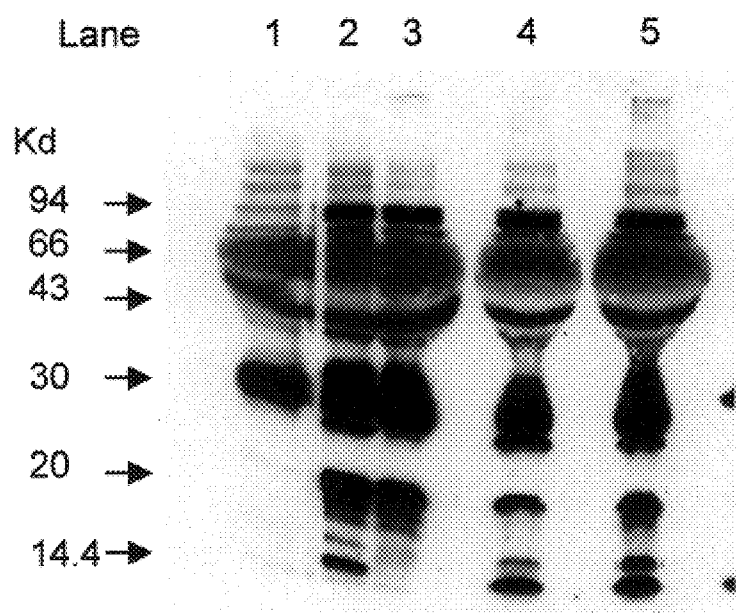
FIG. 2 shows Western blot analysis of synovial fluid from patients with different arthritic conditions using rabbit anti-H741 antibody. Lane 1, Immunoblotting of synovial fluid froma psoriatic arthritis patient (patient #19) in the presence of 50-fold molar excess of peptide H741; Lane 2, Synovial flouid from patient #19; Lane 3, Severe osteoarthritis/rheumatoid arthritis (sample #96020); Lane 4, Moderate RA; Lane 5, Moderate RA; Lane 6, Low mol. wt. markers: 97.4 kDa, 66.3 kDa, 45 kDa, 31 kDa, 21.5 kDa, and 14.4 kDa.
Figure 3:
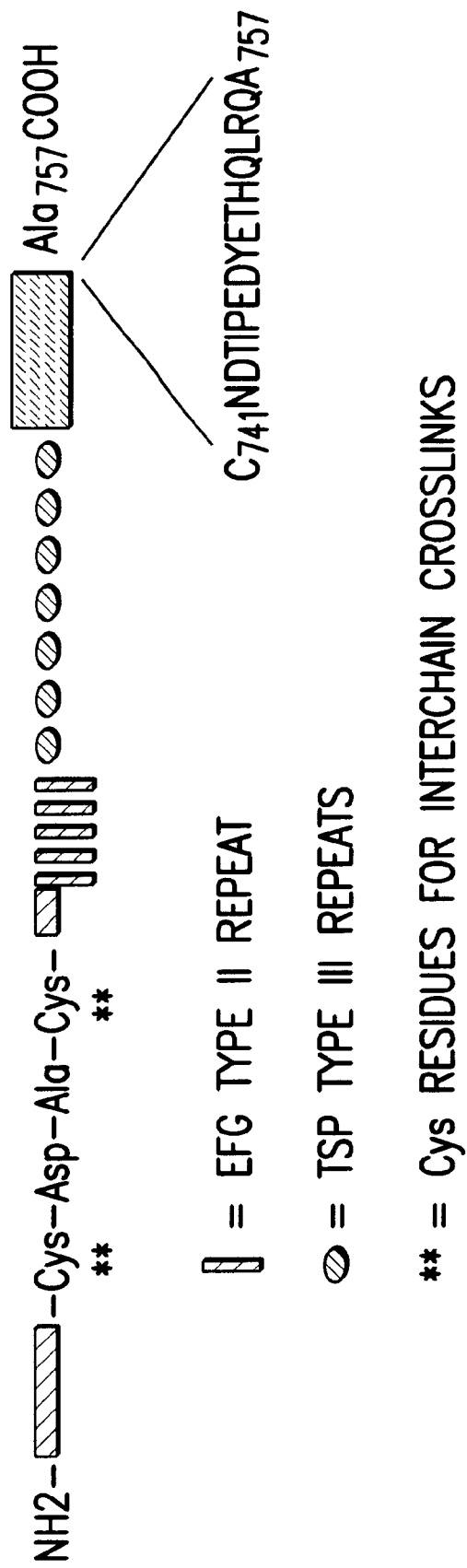
FIG. 3 Schematic representation of monomeric subunit of human COMP: Human COMP consists of N-terminal domain, interchain linking region, EGF and TSP like repeat domains, and C-terminal domain. A synthetic heptadecapeptide to the C-terminal COMP was used for antibody production.
Figure 4:
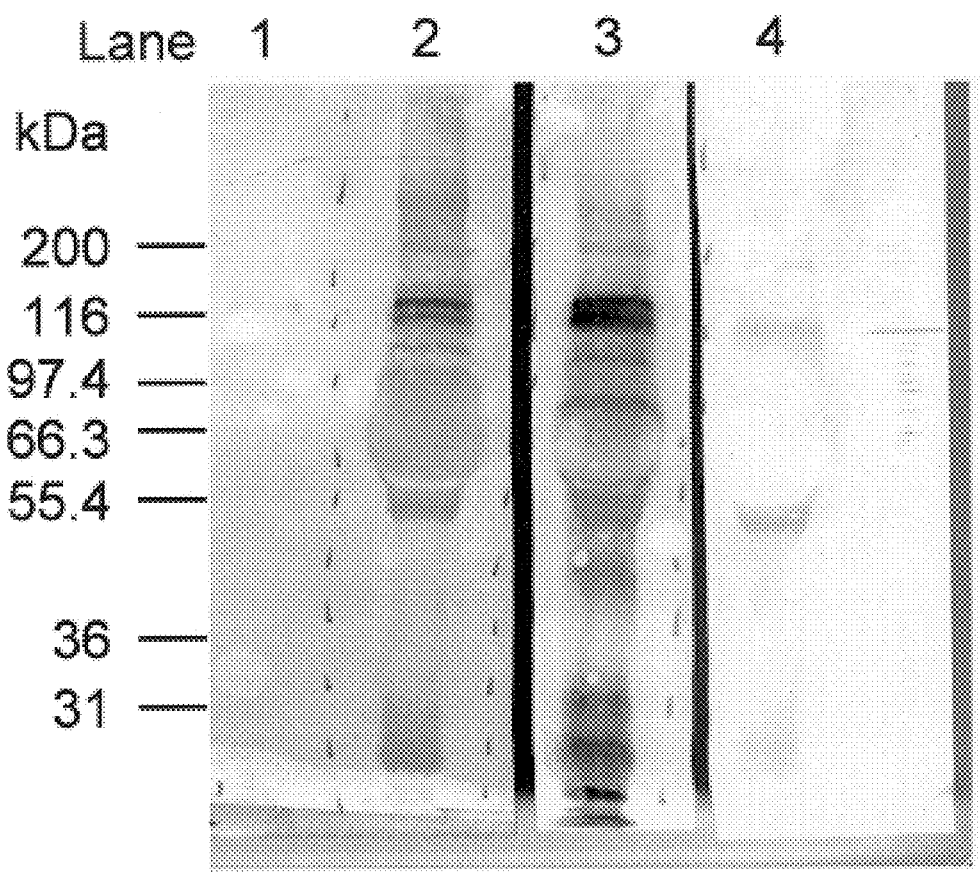
FIG. 4 Comparison of immunoreactive Fragments detected in synovial fluid by Rabbit anti-human COMP and by Rabbit antipeptide antibody in H741: Five microliters per lane of synovial fluid was applied on a 10% SDS-PAGE gel under reducing conditions and electrophoretically blotted onto a nitrocellulose membrane and individual lanes were cut into strips. Lane 2 was analyzed using a polyclonal antibody to COMP, lane 3 was analyzed using antipeptide antibody H741, and lane 4 was analyzed using an unrelated antibody raised in rabbit. Location of molecular weight markers is shown at left.
Figure 5A:
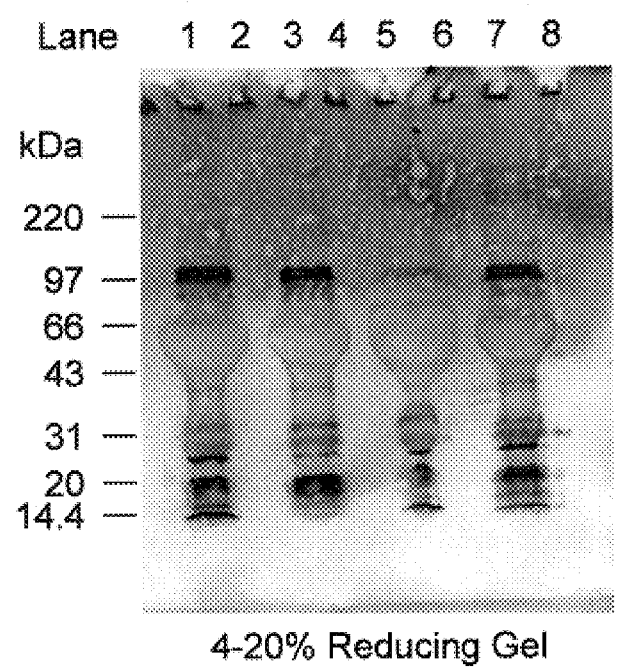
FIG. 5 Western analysis of synovial fluid of rheumatoid (RA) and osteoarthritic patients (OA) using antibody H741: Five microliters per lane of synovial fluid was applied on a 4–20% SDS-PAGE gel under reducing (5A) and non-reducing (5B) conditions. The gels were blotted onto a nitrocellulose membrane and analyzed using antibody H741 (2.5 microgram/milliliter). Lane 1: Mild RA patient; Lane 3: Severe OA patient: Lane 5: Moderate RA patient; Lane 7: severe OA patient.
Figure 5B:
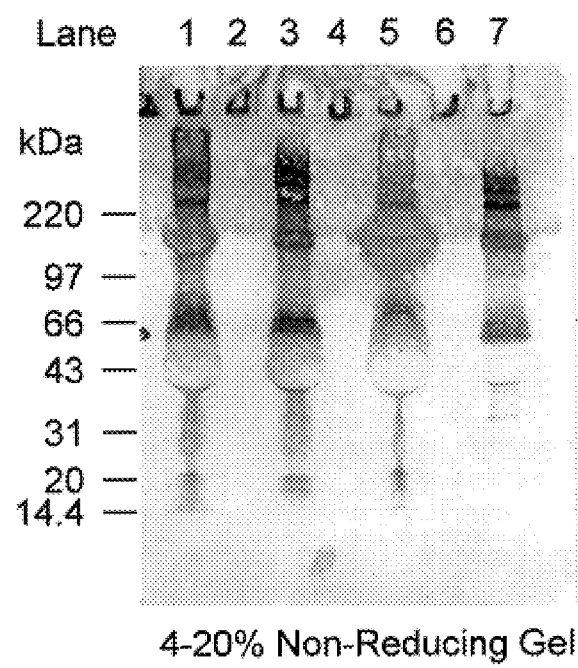

Identification of a Low Molecular Weight Fragment of COMP as a Degradation Product of COMP 10 μl of hyaluronidase from streptomyces treated synovial fluid was mixed with 10 μl of SDS sample buffer containing 10% mercaptoethanol. The samples were boiled for 4 min. and 15 μl was applied onto a 14% SDS-PAGE. After electrophoresis, the proteins were electrophoretically transferred (100 volts, 2 hours at 4° C.) onto a nitrocellulose membrane. The nitrocellulose membrane was stained with 0.2% ponesau S red dye (Sigma Chemical, St. Louis, Mo.) in 1% acetic acid to visualize the protein markers. The markers were marked with a green colored pencil, the blot was washed extensively with PBS and blocked with 2% BSA in PBS at 4° C. for 18 hours. The blot was developed with rabbit antibody H741 as described in Example 3. FIGS. 1 and 2 show the various LMW-COMP fragments that were obtained having apparent molecular weights about 30, 20, 18, 16 and 14 kilodaltons. The most predominant species appears to have a molecular weight of about 20 kilodaltons.

Example 3

Analysis of Human Synovial Fluid for COMP Fragments by Western Immunoblotting

Human synovial fluids were collected in EDTA, serums were prepared from plasma and stored frozen until use. For western blot analysis, synovial fluid was treated with hyaluronidase (Saxne and Heinegard, (1992) Br. J. Rheumatol. 31: 583–591) in the presence of 1 µl of 10 mg/ml PMSF (Phenyl methane sulfonic acid) in drug isopropane for 2 hours at 56° C. and stored frozen until use. For ELISA assay, the synovial fluids or serums are treated with 2 mM Iodoacetamide (Aldrich Chem.) or 2 mM N-ethyl maleimide (Aldrich Chem.). Synovial fluids or serums were selectively precipitated with 30% ammonium sulfate or 20% PEG to enrich low mol. wt. fragments of COMP and then stored at −20° C.

Urine was collected, centrifuged and stored frozen until use.

Twenty microliters of human synovial fluids were mixed 1:1 with SDS-PAGE loading buffer (NOVEX, San Diego, Calif.) containing 10% mercaptoethanol. The samples were boiled for 4 min. and 15 ml applied per lane on a 14% or a 4–12% gradient SDS-PAGE Tris-Gly gel (Novex, Calif.). A separate set of these samples was also prepared for analysis under non-reducing conditions. Molecular weight markers were used to localize the molecular weight of unknowns. After electrophoresis, the samples were electrophoretically transferred onto a nitro-cellulose paper. The paper was treated with 2% bovine serum albumin (BSA) in 10 mM sodium phosphate, 0.15 M NaCl at pH 7.5 (PBS) for 18 hours at 4° C.

The nitrocelluose paper was rinsed with PBS (10 mM sodium phosphate, 0.15 M NaCl at pH 7.2). 5 ml of affinity purified antibody (3.6 mg/ml protein concentrated in stock solution) was diluted to 7 ml in ELISA diluting buffer (20 mM Tris, 0.1 5M NaCl, 0.1% Tween-20, 0.1% thimersol, 0.1% bovine serum albumin) and the solution overlaid on to nitrocellulose membrane. After 1 hour at room temperature, the membrane was washed 4-times (5 min./wash) with ELISA diluting buffer without albumin. The membrane was then incubated with 1 mg of monoclonal antibody to rabbit IgG conjugated to horseradish peroxidase (Sigma Immunochemicals, USA) in 1 ml of ELISA diluting buffer for 1 hour at room temp. The membrane was washed 5-times with ELISA diluting buffer without albumin and 2-times with phosphate buffer saline at pH 7.5. The bound antibody was then detected using ECL or ECF substrate (Amersham Co.). The fragments were quantified using a Molecular Dynamics densitometer (Sunnyvale, Calif.). The same nitrocellulose membrane was then visualized using TMB (Promega, Madison, Wis.) substrate.

Example 4

Quantitation of COMP Fragmentation by ELISA Assay

Several ELISA techniques are used to measure the fragmentation of the COMP protein.

1. Competition ELISA Assay

A 96-well microtiter plate was coated with 0.1 ml/well of 50 ng/ml of antigen (synthetic peptide H741 without the N-terminal cysteine) in PBS for 48 to 72 h at 4° C. The wells were blocked with 300 µl/well of 2% bovine serum albumin (BSA) in PBS for 1.5 h at room temperature (RT). The wells were washed 2-times with ELISA wash buffer (20 mM tris at pH 7.5 containing 0.1 5M NaCl, 0.1% tween-20, 0.1% thimersol), and to each well was added 50 µl of biological fluid (synovial fluid, serum, or urine) diluted 1:10, 1:20, or 1:40 in the assay buffer (ELISA wash buffer containing 0.1% BSA) followed by the addition of 50 µl/well of rabbit anti-COMP peptide antibody at 0.7 µg/ml in the assay buffer. To estimate the concentration of antigenic material in the biological fluid, a standard curve was generated using standards (solutions of known concentrations of antigen). The standards were prepared in the assay buffer to give final concentrations of 1.5 nM, 4.6 nM, 11.5 nM, 34 nM, 46 nM, 115 nM, and 463 nM. It was then assayed, in duplicate, by adding 50 µl/well followed by mixing with 50 µ/well of the rabbit anti-COMP peptide antibody. All samples, standards and synovial fluid samples, were incubated at RT for 2 h., the plate was washed 3-times with the ELISA wash buffer followed by addition of 100 µl/well of goat anti-rabbit IgG antibody conjugated to alkaline phosphatase (Calbiochem, San Diego, Calif.) which was prepared by diluting stock solution 1:3000 in the assay buffer. After 1 h at RT, the plate was washed 3-times with the ELISA wash buffer and the bound antibody detected by adding 100 µl/well of p-nitrophenyl phosphate substrate solution (Sigma, St. Louis, Mo.) and measuring optical density (OD) at 405 nm. A 4-parameter logistic fit of the equation $y=(A-D)/(1+(x/C)^8)+D$, where $y=OD_{405\ nm}$, $x=nM$ H741 was used to obtain a standard curve. The concentration of the antigen in the synovial fluid was then extrapolated using the graph on a Molecular devices microplate reader attached to a Macintosh computer.

Results:

The H741 COMP antigen has been successfully quantified in several synovial fluids from arthritic patients. The following table 1 summarizes the findings.

TABLE 1

| Disease type | Severity | Mean COMP fragment concentration nM H741 |
|---|---|---|
| Osteoarthritis (OA) | Mild | 335 (n = 2) |
|  | Moderate | 113 (n = 6) |
|  | Severe | 189 (n = 8) |
| Rheumatoid | Mild | 236 (n = 2) |
| arthritis | Moderate | 126 (n = 11) |
| (RA) | Severe | 316 (n = 3) |

The data clearly demonstrates that this ELISA assay identifies quantitative differences between in the COMP fragments in the patients at various stages of the disease progression.

2. Sandwich ELISA Assay

Microtiter plates are coated with 1 µg/well of rabbit-anti-peptide H741 antibody in cold for 18 hours. The wells are blocked with 300 ml of 2% BSA in PBS for 2 hours at room temperature. Several dilutions of human synovial fluid or serum or urine in ELISA wash buffer (20 mM Tris, 0.15M NaCl, 0.1% Tween-20, 0.1% thimersol) containing 0.1%

BSA are prepared. One hundred μl of it is added to microtiter plates and incubated for 1 hour at room temp. The samples are washed (4-times) with ELISA washing buffer. One hundred μl of antibody, preferably monoclonal antibody, to human COMP or to peptide H669 or antibody to the isolated 67–80 kDa COMP fragment conjugated to alkaline phosphatase is added to the wells at 1 μg/well and incubated for 1 hour at room temperature. Later, the wells are washed 3-times with the ELISA wash buffer and bound antibody is quantified as described earlier. A standard curve using purified COMP degradation product of molecular weight about 20 kDa is used to quantify the contents in the unknown.

Human synovial fluid or serum is analyzed for total undegraded COMP by an ELISA method published previously (Saxne and Heinegard, (1992) Br. J. Rheumatol. 31: 583–591).

Example 5

Quantification of COMP Fragments in Patients with Arthritic Diseases

In this example, synovial fluid was used as the source of COMP fragments and anti-peptide antibody H741 was used in the analysis. The procedure described above in Examples 3 and 4 may be applied in the analysis of COMP and its fragments in serum and possibly the fragments (only) in the urine.

First, the fragmentation pattern of synovial fluid COMP was determined after 14% SDS-PAGE electrophoresis under reducing conditions followed by western blotting with rabbit-anti peptide H741 antibodies. Depending upon the specimen this antibody detected, only under reducing conditions, several bands that appear at approximate molecular weights of 33-kDa, 30-kDa, 20-kDa, 18-kDa, 16-kDa, and 14.4 kDa. The quantity of immunoreactive material was quantitated by measuring volume of each of the bands by densitometry. The 94 kilodalton protein is the intact COMP. As shown in Table 2, with osteoarthritis the greater the severity of the disease, the greater the number of fragments. In rheumatoid arthritis, the 20 kilodalton fragment was increased with severe disease. This indicates that the type and degree of COMP fragmentation show the staging of the arthritic process. The LWM-COMP markers are not limited to osteoarthritis and rheumatoid arthritis in gouty arthritic conditions and psoriatic arthritis shows high levels of these fragments.

Second, total antigenic COMP was quantified by adding all the volume contents of each of the fragmented immunoreactive COMP (see Examples 3 and 5 above). Total COMP was quantified by COMP ELISA (Saxne and Heinegard, D. (1992) Br. J. Rheumatology 31: 583–591). A table comprising a ratio of fragmented COMP to total COMP allows examination of the extent of cartilage breakdown. In Table 3, total fragmented COMP measured by volume measurements were used to generate such a ratio.

TABLE 3

| Accession # | DSev | Disease Type | # of fragments | Ratio Frg vol/COMP-ELISA |
|---|---|---|---|---|
| 96012 | mild | OA | 3 | 168 |
| 96018 | severe | OA | 5 | 920 |
| 96016 | moderate | RA | 3 | 148 |
| 96017 | moderate | RA | 5 | 363 |
| 96020 | severe | RA/OA | 3 | 612 |
| 96019 |  | Psoriatic | 6 | 921 |

Based on the results shown above, disease severity and the type of disease (psoriatic arthritis) appear to generate a higher ratio of fragmented COMP to total COMP and a greater number of fragments. This suggests that the extracellular matrix of cartilage undergoes significant degradation. Therefore, the objective of the therapy will be to reduce the number of COMP fragments in the synovial fluid (or serum/urine) and lower the ratio of fragmented COMP to total COMP. The ratio of COMP fragments to other synovial fluid components are also a means to evaluate the disease process.

Example 6

Evaluation of Arthritic Condition. Antiarthritic Agents and Chondroprotective Agents 1. Rheumatoid Arthritis Auto-immune arthritis is induced in rabbits by standard protocols (Pettipher et al (1988) Br. J. Pharmacol. 95: 169–176). Synovial fluid is be collected at several intervals as the disease progresses. The synovial fluid is analyzed using an antibody to C-terminal COMP peptide raised in sheep by Western blotting or ELISA.

2. Osteoarthritis

Osteoarthritis is induced in rabbit knees by surgical intervention (Columbo et al, (1983) Arthritis Rheum. 26: 875–86). Synovial fluid, serum, and urine is collected at several intervals as the disease progresses. The analysis of COMP fragment is done as described in Examples 2 and 3.

TABLE 2

| | | | Protein Band of Mol. wt | | | | | | | |
|---|---|---|---|---|---|---|---|---|---|---|
| Accession | DSev | Disease Type | 94-kDa | 33-kDa | 30-kDa | 20-kDa | ~18-kDa | ~16-kDa | ~14-kDa | TOTAL |
| | | | | | | Volume Units | | | | |
| 96012 | mild | OA | 14,349 | — | — | 6,818 | 7,298 | 1,633 | — | 30,098 |
| 96018 | severe | OA | 14,147 | — | 3,599 | 5,382 | 6,366 | 1,438 | 2,813 | 33,745 |
| 96017 | moderate | RA | 8,128 | — | 4,561 | 4,435 | 2,485 | 2,817 | 3,469 | 25,895 |
| 96021 | moderate | RA | 8,330 | — | 9,299 | 3,688 | — | 964 | 5,705 | 27,986 |
| 96022 | moderate | RA | 10,502 | 7,811 | 5,534 | 6,099 | — | 2,501 | 5,591 | 38,038 |
| 96023 | moderate | RA | 1,923 | — | 6,417 | 8,805 | — | 2,010 | 7,200 | 26,355 |
| 96020 | severe | RA/OA | 8,598 | 6,550 | — | 8,159 | 6,232 | — | — | 29,539 |
| 96019 | | Psoriatic | 8,516 | 8,763 | 6,058 | 8,963 | 5,104 | 532 | 3,491 | 41,427 |
| 96024 | | pseudo gor | 10,875 | — | 7,351 | 14,004 | 9,274 | 1,852 | 5,760 | 49,116 |
| 96025 | | gouty arthr | 12,436 | — | 1,894 | 13,523 | 7,014 | 485 | 541 | 35,893 |
| 96026 | | pseudo gor | 11,720 | — | 8,271 | 7,670 | — | 6,226 | 9,102 | 42,989 |
| | | | — | not measurable | | | | | | |

3. Ratio of LMW-COMP Value to KS Value

The synovial fluids from example 4.1, were assayed for KS. The mean KS values (μg/ml) were determined using the established methods of Campion GV et al., Arthritis Rheum. 34(10):1254–1259 1991) and the mean COMP fragment values obtained in accordance with the method of example 4.1, were compared with KS contents to determine the ratio of mean COMP fragment per mean KS value. As shown in Table 4 below, the KS content appears to be similar amongst the groups; however, the ratio of COMP fragment to KS changes as the disease progresses from mild to moderate to severe.

TABLE 4

| Disease type | Severity | COMP µg/ml | LMW-COMP | Mean KS µg/ml | Ratio of COMP/KS µg/ml | Mean LMW-COMP fragment/Mean KS value |
|---|---|---|---|---|---|---|
| Osteo arthritis (OA) | Mild | 86 (n = 2) | 335 (n = 2) | 23 | 3.74 | 14.89 |
|  | Moderate | 54 (n = 6) | 113 (n = 6) | 27 | 2.00 | 4.26 |
|  | Severe | 67 (n = 8) | 189 (n = 8) | 23 | 2.91 | 8.36 |
| Rheumatoid arthritis (RA) | Mild | 62 (n = 2) | 236 (n = 2) | 79 | .78 | 2.99 |
|  | Moderate | 31 (n = 12) | 126 (n = 11) | 31 | 1.00 | 4.06 |
|  | Severe | 46 (n = 3) | 316 (n = 3) | 54 | .85 | 5.85 |

The full-length COMP/KS ratio is less sensitive to disease state than LMW-COMP/KS ratio.

Example 7

Evaluation of Antiarthritic Agents and Chondroprotective Agents in Humans

Synovial fluid was obtained from patients with either osteoarthritis or rheumatoid arthritis. A 20 ul sample of synovial fluid was treated with hyaluronidase, heated and then treated with either a non-reducing buffer or a reducing buffer and then run on an SDS gel as described in Example 3. The presence of COMP and the low molecular weight COMP fragment was measured using the appropriate antibody as described in Example 3. Table 5 shows that the treatment of the arthritis conditions produces less of the LMW-COMP fragment when the treatment is with a strong anti-arthritic compound such as methotrexate or piroxicam.

TABLE 5

| Patient # | Disease Type | Duration | Treatment | LMW-COMP Fragments nM H741 |
|---|---|---|---|---|
| 4559 | OA, Severe | >20 y | NSAID | 188 |
| 4881 | OA, Mild | 1 y | NSAID | 484 |
| 302 | RA, Mild | 8 y | NSAID Methotrexate | 244 |
| 4164 | RA, Mild | 20 y | As above | 146 |
| 4748 | RA, Mild | 10 y | Steroids | 346 |

The progressive treatment of an arthritic conditions is monitored and measured by performing an assay to measure the level of COMP fragment during diagnosis or prior to treatment and comparing it to the level of COMP fragment at various times during the course of treatment. In this way, attending physicians and clinicians can adjust the administration of anti-arthritic agents to optimize treatment and alleviation of the arthritic condition.

---

What is claimed is:

1. An assay to measure the level of low molecular weight cartilage oligomeric matrix protein fragments in the body fluid of a patient comprising:

incubating a solution comprising body fluid obtained from a patient under conditions wherein disulfide bonds in proteins in the body fluid solution are not reduced;

separating low molecular weight cartilage oligomeric matrix protein fragments, wherein the low molecular weight cartilage oligomeric matrix protein fragments have a molecular weight between about 14 kD and 33 kD as determined by 14% sodium dodecyl sulfate polyacrylamide gel electrophoresis, in the solution from undegraded cartilage oligomeric matrix protein in the solution and cartilage oligomeric matrix protein degradation products that are not low molecular weight cartilage oligomeric matrix protein fragments in the solution;

incubating the solution with an antibody that binds to a low molecular weight cartilage oligomeric matrix protein fragment, wherein binding with the antibody will yield antibody-bound low molecular weight cartilage oligomeric matrix protein fragments if low molecular weight cartilage oligomeric matrix protein fragments are present in the body fluid sample; and measuring the amount of antibody-bound low molecular weight cartilage oligomeric matrix protein fragments with molecular weights between about 14 kD and 33 kD.

2. An assay to measure the amount of low molecular weight cartilage oligomeric matrix protein fragments in the body fluid of a patient comprising:

contacting a solution comprising body fluid from a patient with an amount of a reducing agent to reduce disulfide bonds in proteins in the body fluid sample to yield a reducing solution;

separating low molecular weight cartilage oligomeric matrix protein fragments, wherein the low molecular weight cartilage oligomeric matrix protein fragments have a molecular weight between about 14 kD and 33 kD as determined by 14% sodium dodecyl sulfate polyacrylamide gel electrophoresis, in the reducing solution from undegraded cartilage oligomeric matrix protein in the reducing solution and cartilage oligomeric matrix protein degradation products that are not low molecular weight cartilage oligomeric matrix protein fragments in the reducing solution;

contacting the low molecular weight cartilage oligomeric matrix protein fragments from the reducing solution with an antibody that binds to a low molecular weight cartilage oligomeric matrix protein fragment to yield an amount of antibody-bound low molecular weight cartilage oligomeric matrix protein fragments; and measuring the amount of antibody-bound low molecular weight cartilage oligomeric matrix protein fragments with molecular weights between about 14 kD and 33 kD.

3. The assay according to claim 2 wherein the reducing agent is selected from the group consisting of dithiothreitol and mercaptoethanol.

4. The assay according to claim 2 wherein the antibody is an antibody raised against a polypeptide with a sequence selected from the group consisting of SEQ ID NO:1, SEQ ID NO:2, SEQ ID NO:3, and SEQ ID NO:4.

5. The assay according to claim 2 wherein the measuring of the amount of antibody-bound low molecular weight cartilage oligomeric matrix protein fragments comprises employing a technique selected from the group consisting of Western Blotting and enzyme-linked immunosorbent assay.

6. The assay according to claim 2, further comprising contacting the reducing solution with a reducing agent inactivating substance prior to contacting the lowmolecular weight cartilage oligomeric matrix protein fragments from the reducing solution with an antibody; and wherein the measuring of the amount of antibody-bound low molecular weight cartilage oligomeric matrix protein fragments comprises employing an enzyme-linked immunosorbent assay technique.

* * * * *

UNITED STATES PATENT AND TRADEMARK OFFICE
CERTIFICATE OF CORRECTION

PATENT NO.    : 6,589,755 B1
DATED         : July 8, 2003
INVENTOR(S)   : Vishwas Ganu It is certified that error appears in the above-identified patent and that said Letters Patent is hereby corrected as shown below:

<u>Title page,</u>
Item [57], ABSTRACT,
Line 7, change "collectivvly" to -- collectively --.

<u>Column 17,</u>
Line 8, change "lowmo-" to -- low mo- --.

Signed and Sealed this

Thirtieth Day of September, 2003

JAMES E. ROGAN
*Director of the United States Patent and Trademark Office*